United States Patent
Takahashi et al.

(10) Patent No.: US 9,314,788 B2
(45) Date of Patent: Apr. 19, 2016

(54) SPECIMEN IDENTIFICATION AND DISPENSATION DEVICE AND SPECIMEN IDENTIFICATION AND DISPENSATION METHOD

(75) Inventors: Toru Takahashi, Tokyo (JP); Jie Xu, Tokyo (JP); Ken Tsukii, Tokyo (JP)

(73) Assignee: FURUKAWA ELECTRIC CO., LTD., Tokyo (JP)

( * ) Notice: Subject to any disclaimer, the term of this patent is extended or adjusted under 35 U.S.C. 154(b) by 1051 days.

(21) Appl. No.: 13/003,403

(22) PCT Filed: Jul. 9, 2008

(86) PCT No.: PCT/JP2008/062421
§ 371 (c)(1),
(2), (4) Date: Apr. 11, 2011

(87) PCT Pub. No.: WO2010/004627
PCT Pub. Date: Jan. 14, 2010

(65) Prior Publication Data
US 2011/0177489 A1  Jul. 21, 2011

(51) Int. Cl.
*C12Q 3/00* (2006.01)
*C12M 1/36* (2006.01)
(Continued)

(52) U.S. Cl.
CPC .......... *B01L 3/0262* (2013.01); *G01N 35/1016* (2013.01); *B01L 2200/0647* (2013.01);
(Continued)

(58) Field of Classification Search
CPC ................ G01N 1/38; G01N 2001/38; G01N 2001/386; G01N 2035/1032; G01N 35/00584; G01N 35/1016; G01N 35/1081; G01N 35/1011; G01N 35/1083; G01N 35/109; G01N 15/149; G01N 15/1484; G01N 15/1481; G01N 15/1404; G01N 15/1425; G01N 2035/1034; B01L 3/0262; B01L 2200/0647; B01L 2300/0838; B01L 2300/0654
See application file for complete search history.

(56) References Cited

U.S. PATENT DOCUMENTS 6,387,330 B1 *  5/2002  Bova et al. .................... 422/509
2006/0170912 A1  8/2006  Mueth et al.
(Continued)

FOREIGN PATENT DOCUMENTS

EP  1 707 938 A1  10/2006
EP  1 739 402 A1  1/2007
(Continued)

OTHER PUBLICATIONS

Smith, Terrance L. et al. "Inexpensive laboratory-constructed nephelometer." Applied and Environmental Microbiology (1982) 44 1476-1478.*
(Continued)

*Primary Examiner* — Christopher A Hixson
(74) *Attorney, Agent, or Firm* — Oblon, McClelland, Maier & Neustadt, L.L.P.

(57) ABSTRACT

A specimen identification and dispensation device includes an optical measurement device which is an identification part for measuring and identifying optical information on a specimen by emitting exciting light to the specimen being a measurement target dispersed in a liquid flowing through inside of a capillary, a dispensation part for dispensing the identified specimen into wells being sections to be dispensed through a nozzle, and a concentration adjustment part which adjusts the number of the specimens contained in an aliquot solution to a desired number according to the concentration of a sample liquid and the amount of the aliquot solution. The dispensation part is movable three-dimensionally with respect to the identification part and the nozzle.

20 Claims, 17 Drawing Sheets

(51) Int. Cl.
*B01L 3/02* (2006.01)
*G01N 35/10* (2006.01)

(52) U.S. Cl.
CPC .. *B01L2300/0654* (2013.01); *B01L 2300/0838* (2013.01); *G01N 35/1081* (2013.01); *G01N 2035/1034* (2013.01)

(56) References Cited

U.S. PATENT DOCUMENTS

2007/0056351 A1* 3/2007 Curtis et al. ............... 73/1.74
2008/0072664 A1* 3/2008 Hansen et al. ............. 73/61.71

FOREIGN PATENT DOCUMENTS

| JP | 61-35331 | 2/1986 |
| JP | 2003-284544 | 10/2003 |
| JP | 2005-249585 | 9/2005 |
| WO | WO 2005/071386 A1 | 8/2005 |
| WO | WO 2005/103642 A1 | 11/2005 |
| WO | WO 2006/083907 A2 | 8/2006 |

OTHER PUBLICATIONS

LeBlanc, Ludovic et al. "Monitoring the identity of bacteria using their intrinsic fluorscence." FEMS Microbiology Letters (2002) 211 147-153.*

Tatsuro Yamashita, et al., "Basic Theory of FACS (2), Fundamental Theorem and Basic Operations for Sorting", Cell Technology, vol. 16, No. 10, 1997, pp. 1532-1541.

Japanese Office Action issued Dec. 26, 2011 in patent application No. 2007-161928 with English translation.

U.S. Appl. No. 13/342,245, filed Jan. 3, 2012, Takahashi, et al.

* cited by examiner

FIG. 2
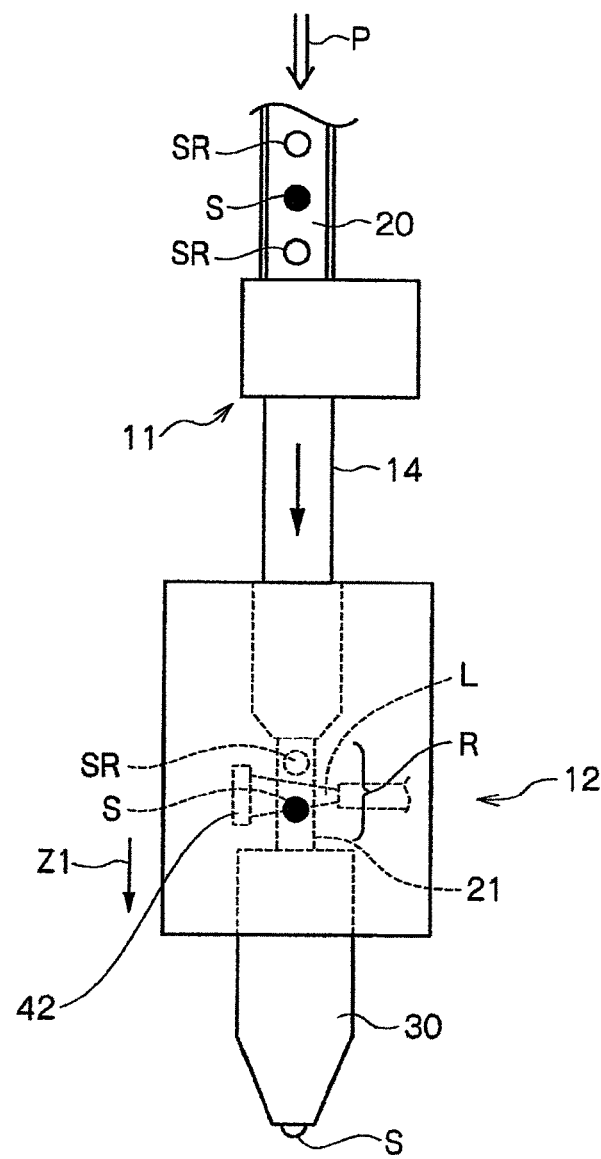
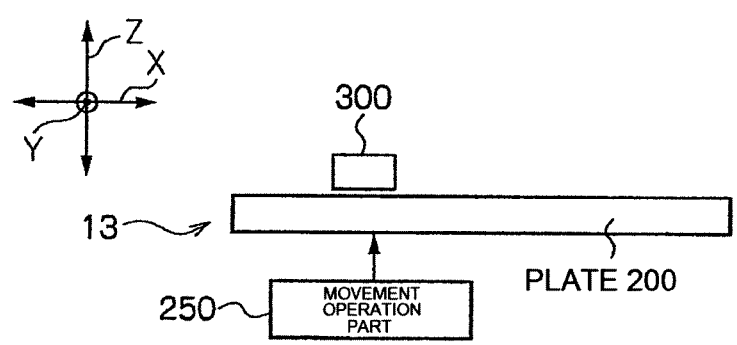

FIG. 16

| | DISPENSATION TARGET CELL | | | DISPENSATION PARAMETER | | | | DISPENSATION RESULT | | | |
|---|---|---|---|---|---|---|---|---|---|---|---|
| | CELL NUMBER (/tube) | LIQUID AMOUNT (μl/tube) | TARGET CELL PRESENCE RATE (/tube) | PRE-DISPENSATION AMOUNT (μl/well) | DISPENSATION AMOUNT (μl/sort) | TARGET CELL DISPENSING NUMBER | LIQUID AMOUNT (μl/well) | SAMPLE DISPENSATION AMOUNT (μl/well) | TARGET CELL PRESENCE RATE (μl/well) | TIME (min) |
| FIRST TIME | 100,000 | 100 | 0.01% | 50 | 3 | 10 | 80 | 75 | 1.33% | 11.1 |
| SECOND TIME | 750 | 80 | 1.33% | 50 | 3 | 10 | 80 | 1 | 100.00% | 8.9 |
| | | | | | | | | | TOTAL | 20.0 |

SPECIMEN IDENTIFICATION AND DISPENSATION DEVICE AND SPECIMEN IDENTIFICATION AND DISPENSATION METHOD

TECHNICAL FIELD

The present invention relates to a specimen identification and dispensation device and a specimen identification and dispensation method. Particularly, the present invention relates to a specimen identification and dispensation device and a specimen identification and dispensation method in which after identification of a specimen is performed by using light information of a separated specimen, the specimen can be dispensed into a predetermined dispensation position without causing contamination and affecting the specimen, and a processing time of a dispensation work can be reduced.

BACKGROUND ART

A technique of identifying a specimen by allowing a liquid in which a specimen (a suspected minute object) such as a cell is dispersed to flow inside a capillary, irradiating the liquid flow with light from a light source, and measuring light information (fluorescence information) of the specimen in the liquid flow was suggested. After identifying the specimen, a dispensation part applies ultrasonic vibration to the specimen to form liquid droplets, and, for example, a charge of several hundred volts is applied. A voltage of several thousand volts is applied from a deflection plate to divide a drop position of each liquid droplet into a positive pole side and a negative pole side, thereby causing dispensation into an arbitrary container (a well) of the dispensation part. [Non-Patent Literature 1] Tatsuro YAMASHITA and Shinichiro NIWA, Cell Technology Vol. 16, No. 10, pp 1532-1541, 1997

DISCLOSURE OF THE INVENTION

Problems to be Solved by the Invention

However, if the specimen such as a cell is dispensed as described above, high frequency vibration and a high voltage of several thousand volts are applied to the small liquid droplet having the specimen therein at the time of dispensation. For this reason, when a living cell is used as a specimen, a death rate of the specimen after dispensation is high, and even though the specimen is alive, the normal condition of the specimen is not certainly guaranteed. Particularly, this has a bad influence on culture and differentiation of a stem cell. Further, since it is indispensable to form the small liquid droplets in the specimen dispensation work, the specimen comes in contact with a large amount of air as well as the ultrasonic wave and the electric charge. Thus, there is fear that the liquid droplets are contaminated, and the specimen is damaged.

There was also a problem in that a work of dispensing a plurality of specimens in the dispensation part requires a lot of dispensation work time since a mechanical movement work (a mechanism movement work) is performed at the time of selecting a dispensation destination among wells. Generally, a dispensation work speed is about 1 sort/sec. For example, in the case of the dispensation work of the target cell in which the total number of cells was 100,000 and a presence rate was 0.01%, the processing time necessary for the dispensation work of all cells was about 100,000 (28 h). Here, the presence rate is referred to as a rate of the number of target cells, as aliquot targets, among all cells.

In order to solve the above problems, it is an object of the present invention to provide a specimen identification and dispensation device and a specimen identification and dispensation method in which after identification of the specimen is performed, the specimen can be dispensed into a predetermined specimen dispensation position without causing contamination and affecting the specimen, and the processing time of the dispensation work can be reduced.

Means for Solving the Problems

In order to solve the above-mentioned conventional problems, the following inventions are provided.

A specimen identification and dispensation device according to a first aspect of the present invention is a specimen identification and dispensation device that dispenses a target specimen as an aliquot target from specimens, which are measurement targets, dispersed in a sample liquid flowing in a flow passage and includes an identification part that measures light information of the specimen by irradiating the specimen with exciting light and identifies the specimen based on the light information of the measured specimen, a dispensation part that dispenses an aliquot solution in which one or more specimens identified by the identification part are dispersed into a dispensation target section through a nozzle, and a concentration adjustment part that adjusts the number of the target specimens as an aliquot object and the number of non-target specimens contained in the aliquot solution to a desired number based on a sample liquid concentration that is a concentration of the number of specimens contained in the sample liquid in which the specimens are dispersed and an amount of the aliquot solution.

A specimen identification and dispensation device according to a second aspect of the present invention is characterized in that, in the specimen identification and dispensation device according to the first aspect, the amount of the aliquot solution is adjusted based on an amount of the sample liquid, an operation time of the dispensation part and the nozzle for dispensing into the dispensation target section through the nozzle, and an injection time of the aliquot solution into the dispensation target section.

A specimen identification and dispensation device according to a third aspect of the present invention is characterized in that, in the specimen identification and dispensation device according to the first or second aspect, the dispensation part dispenses the aliquot solution into the same dispensation target section a predetermined number of times.

A specimen identification and dispensation device according to a fourth aspect of the present invention is characterized in that, in the specimen identification and dispensation device according to any one of the first to third aspects, the identification part identifies the specimen based on a plurality of identification setting conditions, and the dispensation part dispenses into a plurality of dispensation target sections based on the plurality of identification setting conditions for identifying the specimen in the identification part.

A specimen identification and dispensation device according to a fifth aspect of the present invention is characterized in that, in the specimen identification and dispensation device according to any one of the first to fourth aspects, the dispensation part is movable three-dimensionally with respect to the nozzle.

A specimen identification and dispensation device according to a sixth aspect of the present invention is characterized in that, in the specimen identification and dispensation device according to any one of the first to fifth aspects, the dispensation target section is a plurality of wells formed in a plate, a storage liquid to receive the specimen therein is stored in each of the wells, and the aliquot solution containing the specimen ejected from a front end opening part of the nozzle comes into contact with the storage liquid in the well and is dispensed without forming a liquid droplet from the nozzle.

A specimen identification and dispensation device according to a seventh aspect of the present invention is characterized in that, in the specimen identification and dispensation device according to the sixth aspect, the aliquot solution containing the specimen is formed with a hemispherical shape at the nozzle front end, the specimen is a cell, and the storage liquid in the well is a culture solution.

A specimen identification and dispensation device according to an eighth aspect of the present invention is characterized in that, in the specimen identification and dispensation device according to the sixth or seventh aspect, a portion of the nozzle that forms the front end opening part is formed in a manner such that an outer diameter thereof tapers off toward the front end opening part.

A specimen identification and dispensation device according to a ninth aspect of the present invention is characterized in that, in the specimen identification and dispensation device according to any one of the first to eighth aspects, a flow passage of the nozzle is larger than a flow passage in the identification part.

A specimen identification and dispensation device according to a tenth aspect of the present invention is characterized in that, the specimen identification and dispensation device according to any one of the first to ninth aspects further includes a supply part that separates the specimen, disperses the specimen in the sample liquid, and supplies the specimen to the identification part, in which a flow passage of the specimen formed by the identification part and the nozzle is formed in the form of a straight line until the specimen is dispensed into the dispensation target section.

A specimen identification and dispensation device according to an eleventh aspect of the present invention is characterized in that, the specimen identification and dispensation device according to any one of the first to tenth aspects further includes a resupply part that supplies a liquid containing the target specimen in the dispensation target section to the supply part as the sample liquid, in which a presence rate that is a rate of a total number of the target specimens to a total number of the specimens contained in the sample liquid in the supply part is adjusted.

A specimen identification and dispensation device according to a twelfth aspect of the present invention is characterized in that, in the specimen identification and dispensation device according to any one of the first to eleventh aspects, when the concentration of the sample liquid containing the target specimen therein is within a predetermined range of concentration area, the concentration adjustment part adjusts the number of the specimens contained in the aliquot solution to one, and the dispensation part dispenses the aliquot solution in which one of the target specimens is dispersed to one of the dispensation target sections.

A specimen identification and dispensation method according to a first aspect of the present invention is a specimen identification and dispensation method of dispensing a target specimen as an aliquot target from specimens, which are measurement targets, dispersed in a sample liquid flowing in a flow passage, including: (a) a supply step of separating the specimen, and dispersing and supplying the specimen into the sample liquid, (b) an identification step of measuring light information of the specimen by irradiating the specimen with exciting light and identifying the specimen based on the light information of the measured specimen, (c) a concentration adjustment step of adjusting the number of the specimens in an aliquot solution in which one or a plurality of specimens identified in the identification step (b) are dispersed, and (d) a dispensation step of dispensing the aliquot solution, which is identified through the identification step (b) and adjusted in number through the concentration adjustment step (c), into a dispensation target section through a nozzle, in which the concentration adjustment step (c) can adjust the number of the target specimens being an aliquot object and the number of non-target specimens in the aliquot solution to desired numbers, based on the concentration of the sample liquid which means the number of specimens dispersed in the sample liquid and the liquid amount of the aliquot solution.

A specimen identification and dispensation method according to a second aspect of the present invention is characterized in that, in the specimen identification and dispensation method according to the first aspect, the amount of the aliquot solution is adjusted based on a mechanical operation time of the dispensation step (c) of dispensing into the dispensation target section through the nozzle and an injection time of the aliquot solution required for injecting the aliquot solution into the dispensation target section.

A specimen identification and dispensation method according to a third aspect of the present invention is characterized in that, in the specimen identification and dispensation method according to the first or second aspect, the dispensation step (d) is to dispense the aliquot solution into the same dispensation target section a predetermined number of times.

A specimen identification and dispensation method according to a fourth aspect of the present invention is characterized in that, in the specimen identification and dispensation method according to any one of the first to third aspects, the identification step (b) includes is to identify the specimen based on a plurality of identification setting conditions, and the dispensation step (d) is to perform dispensing into a plurality of dispensation target sections based on the plurality of identification setting conditions for identifying the specimen in the identification step (b).

A specimen identification and dispensation method according to a fifth aspect of the present invention is characterized in that, the specimen identification and dispensation method according to any one of the first to fourth aspects further includes (e) a resupply step of supplying a liquid containing the target specimen in the dispensation target section to the supply step (a) as the sample liquid, in which a presence rate that is a rate of a total number of the target specimens to a total number of the specimens contained in the sample liquid in the supply step (a) is adjusted.

A specimen identification and dispensation method according to a sixth aspect of the present invention is characterized in that, in the specimen identification and dispensation method according to any one of the first to fifth aspects, when the concentration of the sample liquid containing the target specimen is within a predetermined range of concentration area, the concentration adjustment step (c) is to adjust the number of the specimens in the aliquot solution to one, and the dispensation step (d) is to dispense the aliquot solution in which one of the target specimens is dispersed to one of the dispensation target sections.

Effects of the Invention

According to the present invention, after identification of the specimen contained in the liquid flowing out from the front end of the dispensation nozzle is performed, the specimen can be dispensed into the dispensation position from the nozzle without forming the liquid droplet. Particularly, the delicate living cells such as stem cells are not damaged and the survival rate of the living cells can be improved. Further, it is possible to positively influence culture and differentiation of the stem cell, and thus it plays a very important role in putting regeneration medicine of the stem cell into practical use. Further, the specimen can be rapidly dispensed into a predetermined specimen dispensation position without causing contamination and having an influence on the specimen.

By concentrating the sample liquid in a stepwise fashion, that is, by increasing the presence rate of the target specimen to make the appropriate concentration (the sample liquid concentration) of the specimen contained in the sample liquid and then dispensing the target specimen one by one, a time of the mechanism movement work, the work consuming a lot of time, in the dispensation process can be reduced. Therefore, a time of the dispensation work can be reduced.

BRIEF DESCRIPTION OF THE DRAWINGS

FIG. 2 is a view illustrating a supply part, an identification part, and a dispensation part.

FIG. 16 illustrates a result of a dispensation process of an embodiment example.

EXPLANATION OF LETTERS AND NUMBERS

Figure 1:
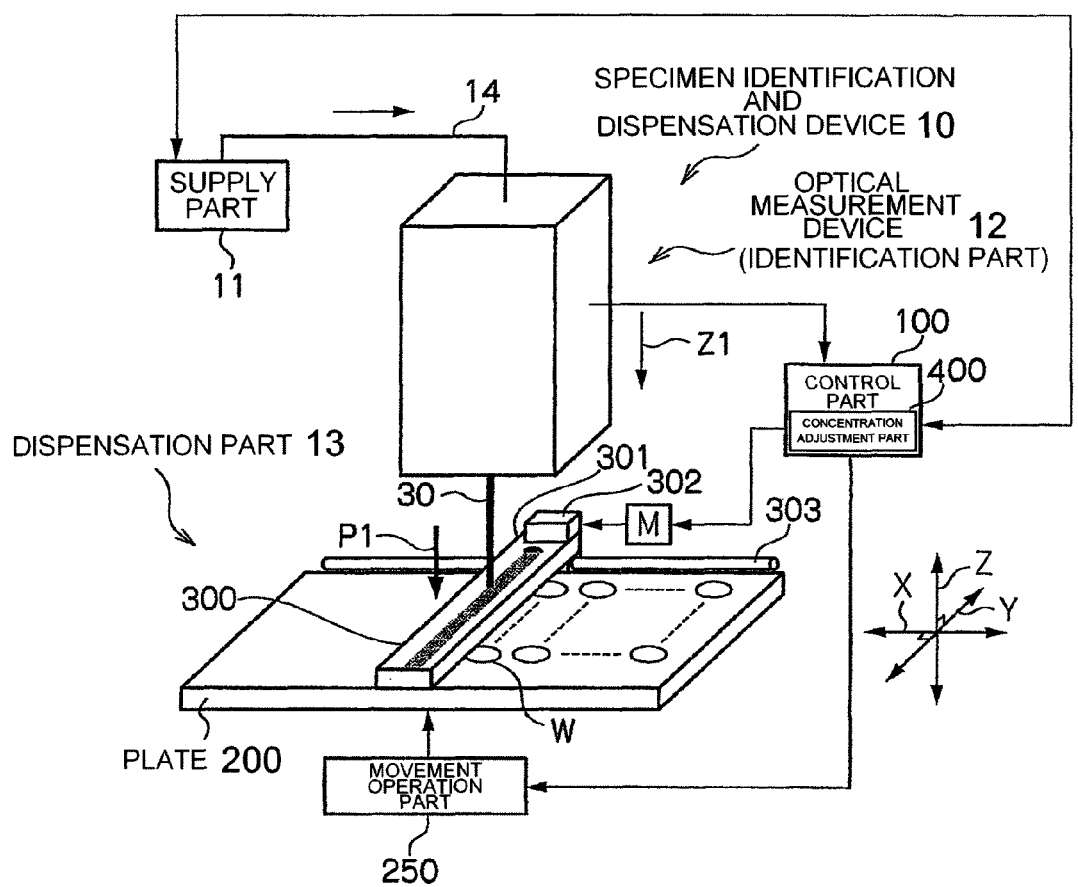
FIG. 1 is a perspective view illustrating an exemplary embodiment of a specimen identification and dispensation device of the present invention.

10: Specimen identification and dispensation device
11: Supply part
12: Optical measurement device
13: Dispensation part
21: Capillary (example of flow passage)
30: Nozzle
41: Laser light source (example of light source)
55: Front end opening part
60: Taper part of nozzle
100: Control part
150: Liquid
160: Waste liquid
200: Plate (culture plate)
250: Movement operation part
300: Waste liquid tank
400: Concentration adjustment part
S: Specimen (sample)
W: Well

BEST MODE FOR CARRYING OUT THE INVENTION

Exemplary embodiments of the present invention will be described with reference to the accompanying drawings. The exemplary embodiments described below are provided for explanation and do not limit the scope of the present invention. Thus, those who skilled in the art would understand that exemplary embodiments in which each or all of components are replaced with equivalent or equivalents thereof may be employed, it is apparent that those also fall with the scope of the present invention.

FIG. 1 is a perspective view illustrating an exemplary embodiment of a specimen identification and dispensation device of the present invention. FIG. 2 illustrates the specimen identification and dispensation device of FIG. 1 in further detail.

Referring to FIG. 1, the specimen identification and dispensation device 10 includes a specimen supply part 11, an optical measurement device 12 as a specimen identification part, a specimen dispensation part 13, a control part 100 including a specimen concentration adjustment part 400, and a specimen resupply part (not shown). The specimen is also called a fine object or a sample, and a plurality of specimens is dispersed in a liquid. The specimen identification and dispensation device 100 is also called a flow cytometer.

The specimen supply part 11 illustrated in FIG. 1 separates specimens S and SR and supplies them to the optical measurement device 12 via a tube 14. The liquid forms a sample flow for carrying the specimens S and SR. The optical measurement device 12 identifies the specimens S and SR by irradiating exciting light, for example, from a laser light source to the specimens S and SR that pass through a capillary as a flow passage in a Z1 direction and receiving fluorescence information of the specimens S and SR.

The dispensation part 13 illustrated in FIG. 1 injects a plurality of identified specimens S into a well (an example of a container) W located at a certain dispensation target position. The specimen S is a target specimen to be dispensed into the well W, and the specimen SR is a non-target specimen that is to be discarded. The control part 100 of FIG. 1 adjusts the concentration of the specimen, analyzes the fluorescence information measured in the optical measurement device 12, and controls the dispensation part 13.

For example, the specimen supply part 11 illustrated in FIG. 1 supplies the specimens S and SR to the optical measurement device 12 via the tube 14 together with a sample liquid 20 as illustrated in FIG. 2.

In the optical measurement device 12, a sample flow containing the specimens S and SR therein and a sheath flow surrounding the sample flow, flow inside a capillary 21. Exciting light L from the laser light source is irradiated onto the specimens S and SR that pass through, so that the specimens S and SR produce, for example, the fluorescence information. The fluorescence information is received by a light receiving part 42. The fluorescence information generated from the specimens S and SR is analyzed by the control part 100 of FIG. 1. The specimens S and SR analyzed by the control part is dispensed into a certain well W or discarded into a waste liquid tank 300 without forming liquid droplets through a nozzle 30.

The concentration adjustment part 400 of the control part 100 illustrated in FIG. 1 adjusts the concentration of a sample liquid which means the concentration (in number) of specimens S and SR contained in the sample liquid 20 that is supplied from the supply part 11 to the optical measurement device 12. It further adjusts the amount of the aliquot solution that is to be dispensed into an arbitrary well W of the dispensation part 13 through the nozzle 30 and dispenses an arbitrary number of specimens S and SR into the well W. Here, the aliquot solution, which is to be dispensed into the well is configured to contain at least one specimen S, based on the analysis result of the fluorescence information measured in the optical measurement device 12.

The amount of the aliquot solution is adjusted based on a flow amount of the sample liquid 20 to be supplied by the supply part 11, an operation time of the dispensation part 13, an operation time of the nozzle 30, and an injection time of the aliquot solution into the well W. In FIG. 1, since the dispensation work is performed by the dispensation part 13 moving three-dimensionally with respect to the nozzle 30, the operation time of the dispensation part 13 is used as the adjustment factor. However, if the nozzle 30 moves, a movement time of the nozzle 30 is used as the adjustment factor instead of the operation time of the dispensation part 13. If the nozzle 30 and the dispensation part 13 move together, the movement time of the nozzle 30 and the dispensation part 13 is used as the adjustment factor.

The control part 100 illustrated in FIG. 1 controls the dispensation part 13 and may dispense the specimens S or SR into an arbitrary well W through the nozzle 30 in the dispensation work or discard the specimens S or SR into the waste liquid tank 300. At this time, dispensation into the same well W may be performed a given number of times. The specimens S or SR may be identified based on a plurality of identification setting conditions and dispensed into a plurality of wells W based on the identification setting conditions. For example, when setting 1 means that setting of the exciting light L from the laser light source is a voltage of 1 to 2 volts and setting 2 means a voltage of 3 to 5 volts, the specimen S measured under the condition of setting 1 may be dispensed into a well W1, and the specimen S measured under the condition of setting 2 may be dispensed into a well W2.

The resupply part supplies the specimens S or SR in the well W of the dispensation part 13 of FIG. 1 to the supply part 11 of FIG. 1 by using, for example, the nozzle.

Figure 3:
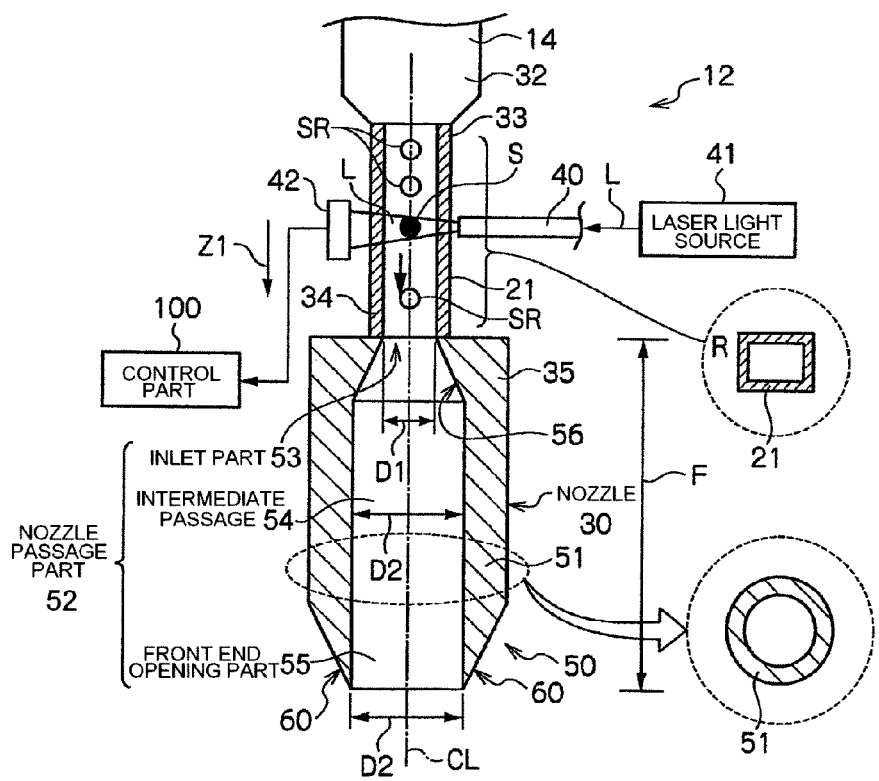
FIG. 3 is a view illustrating a capillary and a nozzle.

FIG. 3 illustrates an example of structures of the capillary 21 and the nozzle 30. A connection part 32 of the tube 14 illustrated in FIG. 3 is connected to one end 33 of the capillary 21, and the other end 34 of the capillary 21 is connected to one end 35 of the nozzle 30. The capillary 21 and the nozzle 30 form a flow passage of a straight line form that allows the specimen S to flow.

As indicated by a range R illustrated in FIG. 3, the capillary 21 is a hollow member whose inner diameter is constant along an axial direction CL and is made of transparent glass or plastic of a straight line form. A cross-sectional shape of the capillary 21 is, for example, a rectangular shape.

An optical fiber 40 is disposed at a position corresponding to the capillary 21. The exciting light L emitted from a laser light source 41 is irradiated onto the specimen S that passes through the inside of the capillary 21 by the optical fiber 40.

Next, the structure of the nozzle 30 illustrated in FIG. 3 will be explained.

The nozzle 30 is a cylindrical member and has one end 35, the other end 50, and an intermediate part 51. The nozzle 30 has a nozzle passage part 52 extending along the axial direction CL. The nozzle passage part 52 includes an inlet part 53, an intermediate passage 54, and a front end opening part 55. An inner diameter D1 of the inlet part 53 is smaller than an inner diameter D2 of the intermediate passage 54 and an inner diameter D2 of the front end opening part 55. Thus, a bugle-shaped part 56 is formed along the Z1 direction between the inlet part 53 and the intermediate passage 54. The intermediate passage 54 and the front end opening part 55 are passage parts having the inner diameter D2 that is constant.

Employing the above-described structure of the nozzle can decrease the flow velocity of the liquid containing the specimen S that is directed toward the intermediate passage 54 from the inlet part 53 since the inner diameter gradually increases in the bugle-shaped part 56. Thus, even though the specimen S such as the living cell flows into the nozzle 30, the specimen S can be prevented from being damaged by the pressure generated by the flow velocity.

In FIG. 3, as the range R of the capillary, for example, one side of a cross section is 20 mm. The length F of the nozzle 30 is, for example, 70 mm to 80 mm. The inner diameter D2 of the nozzle 30 is, for example, 400 μm, and an inside dimension is 150 μm in vertical length and 300 μm in horizontal length.

Figure 4:
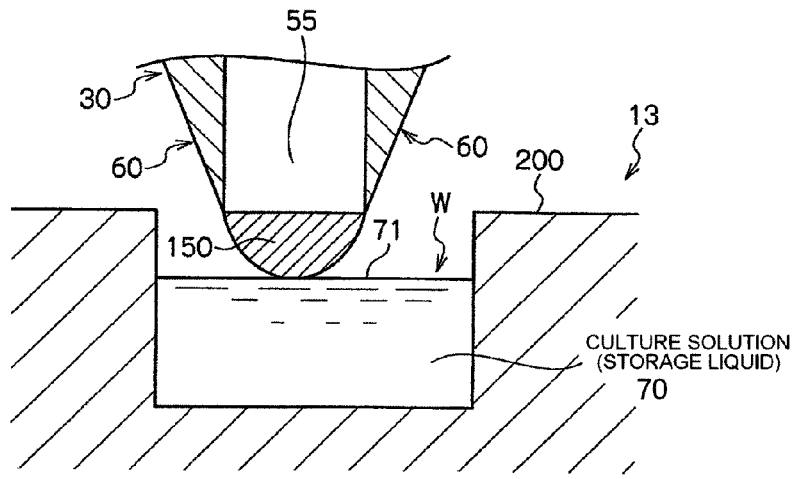
FIG. 4 is a view illustrating a front end part of a nozzle and a well.

As illustrated in FIGS. 3 and 4, a taper part 60 of the other end 50 of the nozzle 30 has a shape tapered toward an outlet 55. Further, as illustrated in FIG. 4, the front end opening part 55 of the taper part 60 of the nozzle 30 allows a liquid droplet 150 of a hemispherical shape that contains the identified specimen S therein to come into contact with a surface 71 of a culture solution 70. In a state in which the front end opening part 55 of the taper part 60 of the nozzle 30 does not come into direct contact with the culture solution 70 in the well W, the specimen S is dispensed into the culture solution 70 in the well W. Thus, when the taper part 60 of the nozzle 30 enters the inside of the well W of the plate 200 of the dispensation part 13, the size of the taper part 60 that has entered the inside of the well W can be reduced as compared with a nozzle having a shape other than a taper shape, thereby preventing the specimen and the culture solution from being contaminated. The liquid droplet may not drop like a liquid droplet (for example, a liquid droplet 1002 in FIG. 17).

As illustrated in FIGS. 1 and 2, in the capillary 21 and the nozzle 30 of the optical measurement device 12, the liquid containing the specimen S flows straight along the Z1 direction in the form of the straight line. Thus, a change in flow velocity of the liquid containing the specimen S therein is small, and the flow velocity can be stabilized.

Next, the dispensation part 13 will be explained with reference to FIG. 1.

The dispensation part 13 of FIG. 1 includes a culture plate (hereinafter, referred to as "plate") 200, a movement operation part 250, and a waste liquid tank 300.

The plate 200 is disposed in an X-Y plane formed by an X-axis direction and a Y-axis direction. The plate 200 includes a plurality of wells W, and a plurality of wells W is disposed in the X-axis direction and the Y-axis direction in the form of a matrix at a predetermined pitch. As illustrated in FIG. 4, the culture solution 70 as an example of a storage liquid is stored in each of the wells W.

The waste liquid tank 300 is disposed on the plate 200 in parallel with the plate 200 along the Y-axis direction.

Figure 5:
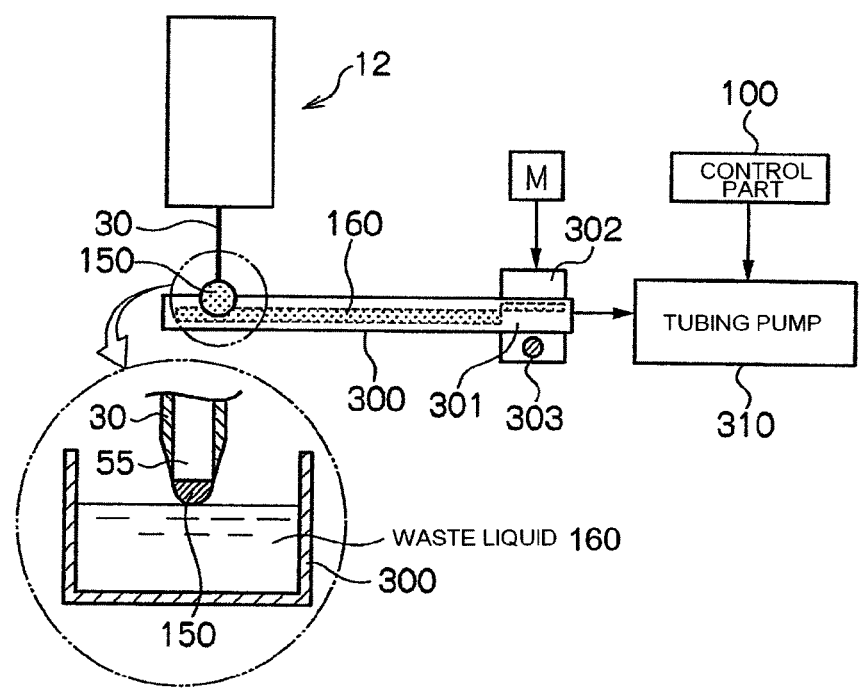
FIG. 5 is a view illustrating a state in which a nozzle approaches a waste liquid tank of a dispensation part.

An example of a structure of the waste liquid tank 300 is illustrated in FIG. 5, and the waste liquid tank 300 has a gutter-shaped member having a U-shaped cross section. One end 301 of the waste liquid tank 300 is fixed to a holder 302, and the holder 302 is movable in the X-axis direction along a guide bar 303. The guide bar 303 is fixed to the plate 200 along the X-axis direction in the lateral part of the plate 200

As an apparatus for moving and positioning the waste liquid tank 300 in the X-axis direction, for example, a mechanism using a motor and a lead screw may be used. In this case, an operation of a motor M is controlled by an instruction of the control part 100. The lead screw is disposed in parallel with the guide bar 303. As the lead screw rotates by an operation of the motor M, the waste liquid tank 300 moves in the X-axis direction and is positioned.

As illustrated in FIG. 5, the waste liquid tank 300 is used to discard the liquid 150 containing the specimen ejected from the nozzle 30 into a waste liquid 160 according to a need. At this time, when the liquid 150 ejected from the front end opening part 55 contains the unnecessary specimen SR, the liquid 150 oozing from the nozzle front end comes in contact with the surface of the waste liquid 160 and is discarded.

As illustrated in FIG. 5, the waste liquid 160 is slowly drained from the waste liquid tank 300 by an operation of a tubing pump 310, and the waste liquid 300 is typically filled with the waste liquid 160. The waste liquid is certainly absorbed by the tubing pump 310 not to overflow from the waste liquid tank 300. Thus, the waste liquid does not leak from the waste liquid tank 300.

Figure 6:
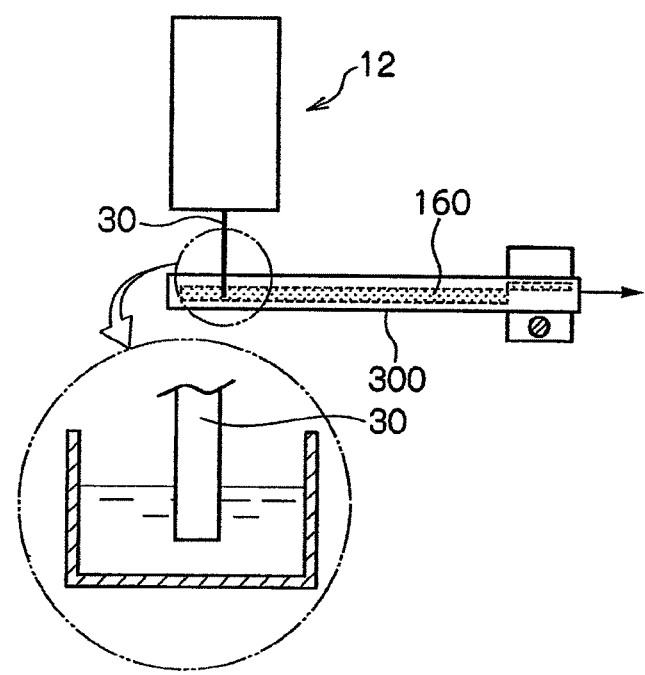
FIG. 6 is a view illustrating a state in which a nozzle is immerged into a waste liquid tank of a dispensation part.

On the other hand, if the nozzle 30 is immersed into the waste liquid 160 as in a comparative example illustrated in FIG. 6, the nozzle 30 comes in direct contact with the waste liquid 160. For this reason, when the specimen S is dispensed into the well W by using the nozzle later, the culture solution in the well W may be contaminated through the nozzle 300. However, according to the exemplary embodiment of the present invention, the front end outlet part 55 of the nozzle 30 does not come in contact with the waste liquid 160 in the waste liquid tank 300. Thus, it is possible to prevent contamination of the culture solution in the well W.

The movement operation part 250 illustrated in FIG. 1 can move and position the plate 200 in the X-axis direction, the Y-axis direction, and the Z-axis direction. The X-axis direction (a first direction), the Y-axis direction (a second direction), and the Z-axis direction (a third direction) are orthogonal to each other. In FIG. 1, the Z-axis direction is the vertical direction. As the movement operation part 250, for example, a typically used three-axis movement table such as an X-Y-Z table may be used.

Next, an example of an operation of the dispensation part 13 will be explained with reference to FIG. 1 and FIGS. 7 to 12.

FIG. 1 illustrates a standby state of the specimen identification and dispensation device 10. The nozzle 30 is disposed below the optical measurement device 12 toward the Z1 direction. The nozzle 30 is disposed at a position corresponding to the waste liquid tank 300. The waste liquid tank 300 is positioned at a standby position in the center of the plate 200 in the X-axis direction.

Figure 7:
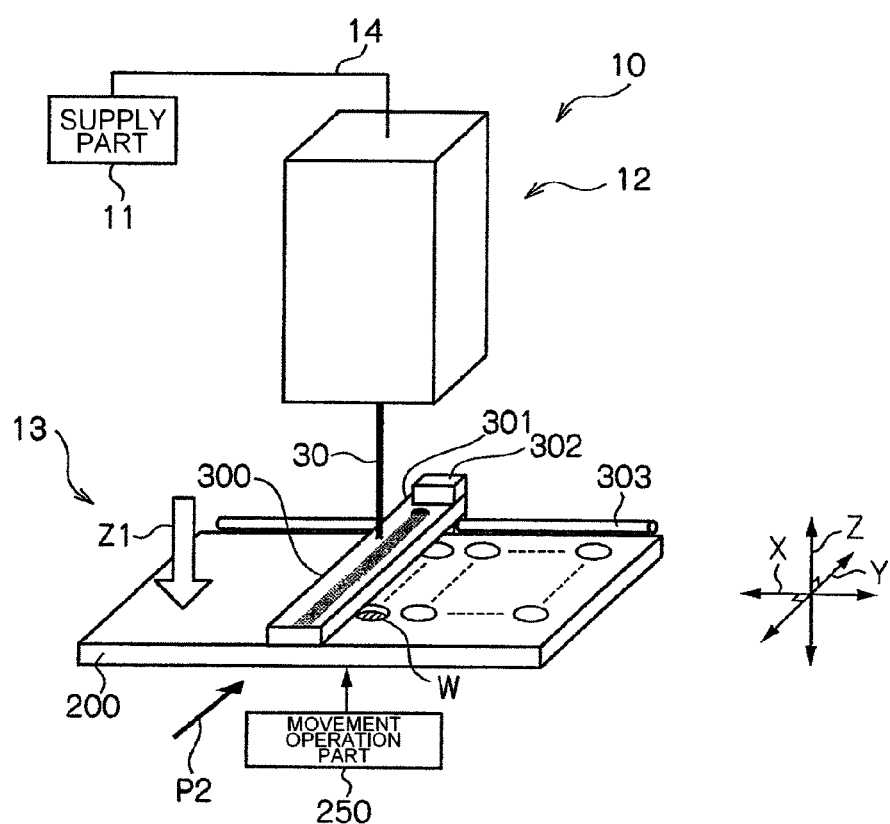
FIG. 7 is a view illustrating a state in which a waste liquid tank evacuates from a standby position of FIG. 1.

FIG. 7 illustrates a state in which the waste liquid tank 300 moved down and evacuated from the standby position P1 of FIG. 1. As the movement operation part 250 operates by an instruction of the control part 100, the plate 200 and the waste liquid tank 300 integrally move down in the Z1 direction and are positioned at an evacuation position P2.

Figure 8:
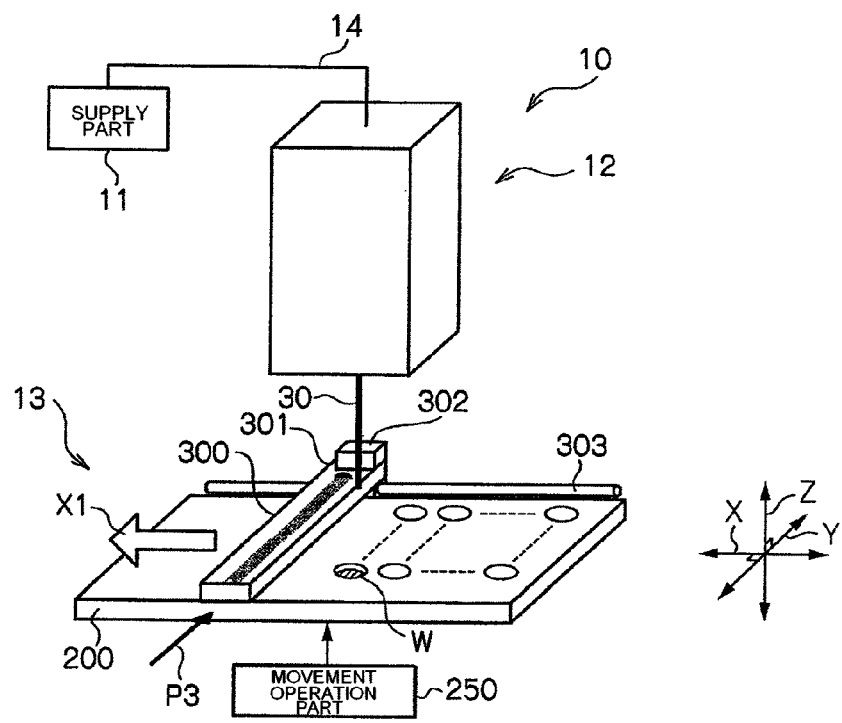
FIG. 8 is a view illustrating a state a state in which a waste liquid tank further evacuates from an evacuation position P2 of FIG. 7 in an X1 direction.

FIG. 8 illustrates a state a state in which the waste liquid tank 300 further evacuated from the evacuation position P2 of FIG. 7 in the X1 direction. As the movement operation part 250 operates by an instruction of the control part 100, the waste liquid tank 300 moves in the X1 direction (the left direction in the paper plane in FIG. 8) with respect to the plate 200 and is positioned at an evacuation position P3. Thus, the waste liquid tank 300 is at a position distant from the nozzle 30.

Figure 9:
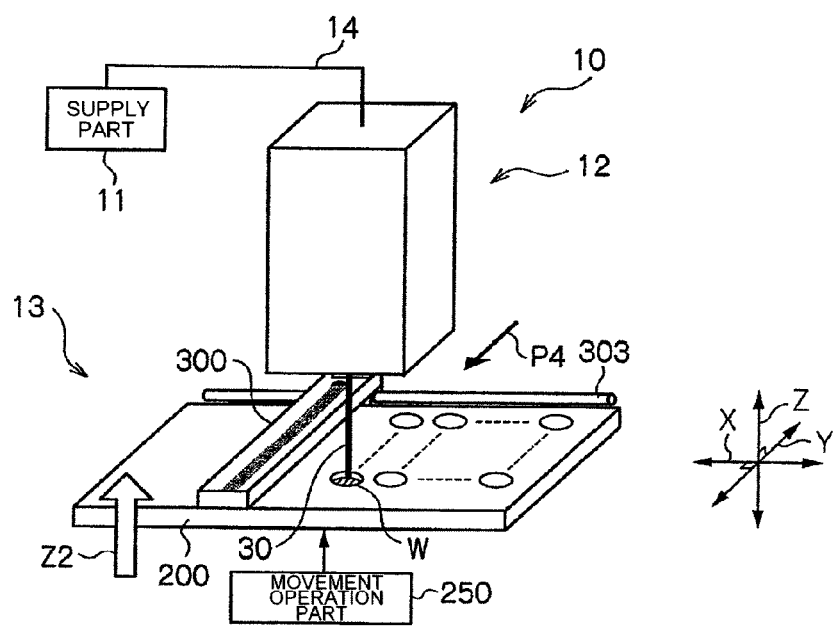
FIG. 9 is a view illustrating a state in which a plate moves up in a Z2 direction.

Next, FIG. 9 illustrates a state in which the plate 200 and the waste liquid tank 300 moved up in a Z2 direction. When the movement operation part 250 operates according to an instruction of the control part 100, the plate 200 and the waste liquid tank 300 are moved up in the Z2 direction and positioned at a dispensation position P4. Thus, as illustrated in FIG. 4, the liquid 150 oozing from the front end opening part 55 of the nozzle 30 comes in contact with the culture solution 70 in the selected well W, so that the liquid 150 containing the specimen S is dispensed into the well W. At this time, the other end (the lower end) 50 of the nozzle 30 has a taper shape, and the other end 50 does not come in direct contact with the culture solution 70. Thus, contaminated substances can be certainly prevented from getting mixed into the culture solution 70 and the specimen S from the nozzle 30 side.

Figure 10:
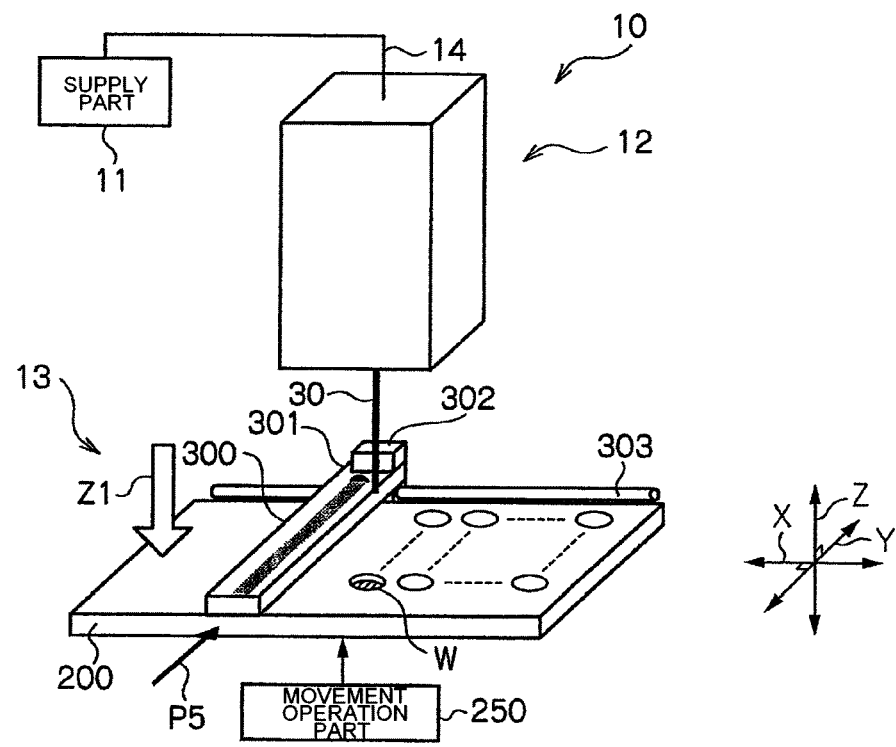
FIG. 10 is a view illustrating a state in which a plate moves down in a Z1 direction again.

FIG. 10 illustrates a state in which the plate 200 and the waste liquid tank 300 moved down in the Z1 direction again. As the movement operation part 250 operates by an instruction of the control part 100, the well W is position at a falling position P5 distant from the nozzle 30.

Figure 11:
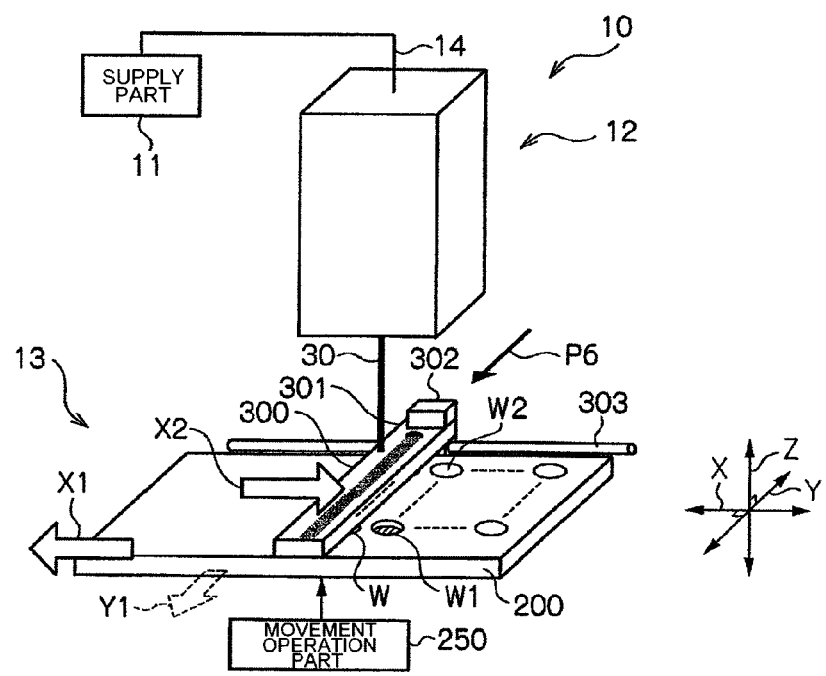
FIG. 11 is a view illustrating a state in which a waste liquid tank is positioned at a standby position P6 below a nozzle again.

FIG. 11 illustrates a state in which the waste liquid tank 300 is positioned at a standby position P6 below the nozzle 30 again. As the movement operation part 250 operates by an instruction of the control part 100, the waste liquid tank 300 moves in an X2 direction and moves toward the standby position P6. At the same time, the plate 200 moves along the X1 direction reverse to the X2 direction by an arrangement pitch of the well. Thus, the nozzle 30 is relatively positioned above an arbitrary well W1 that is at a next position. The waste liquid tank 300 moves in the X2 direction, and at the same time, the plate 200 moves in the X1 direction by the arrangement pitch of the well. Thus, a time required to relatively position the nozzle 30 above the well W1 of the next candidate can be reduced.

Figure 12:
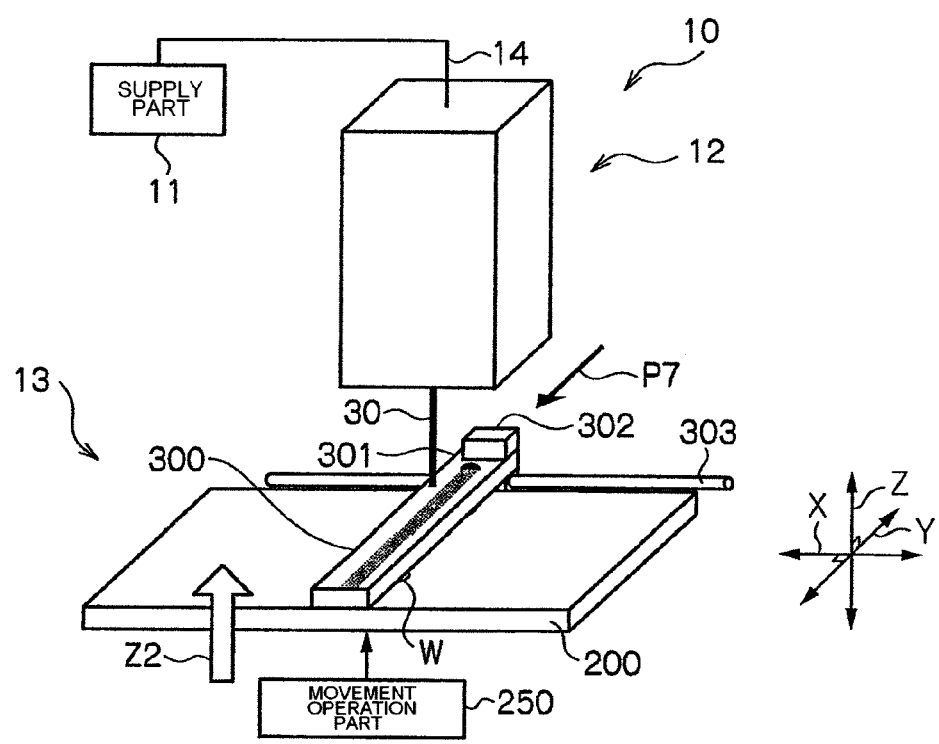
FIG. 12 is a view illustrating a standby state in which a plate and a waste liquid tank moved up in a Z2 direction.

FIG. 12 illustrates a standby state in which the plate 200 and the waste liquid tank 300 moved up in the Z2 direction. When the movement operation part 250 operates according to an instruction of the control part 100, the plate 200 and the waste liquid tank 300 are moved up in the Z2 direction to be positioned at a standby position P6.

The nozzle 30 can dispense the liquid 150 into the well, at an arbitrary position, on the plate 200 by performing a series of such operations. In FIG. 11, in order to dispense the liquid 150 into the well W2 other than the well W1, by operating the movement operation part 250 according to an instruction of the control part 100, the plate 200 and the waste liquid tank 300 move in the Y1 direction by the arrangement pitch of the well and are positioned. The waste liquid tank 300 moves by the movement of the Z-axis direction together with the plate 200. However, when the waste liquid tank 300 moves in the X-axis direction, the waste liquid tank 300 may move and is positioned separately from the plate 200. The nozzle 30 does not move, and a position of the nozzle 30 is fixed. Instead, the units of the plate 200 and the waste liquid tank 300 of the dispensation part 13 move along the X-axis direction, the Y-axis direction, and the Z-axis direction of the movement operation part 250.

Figure 17:
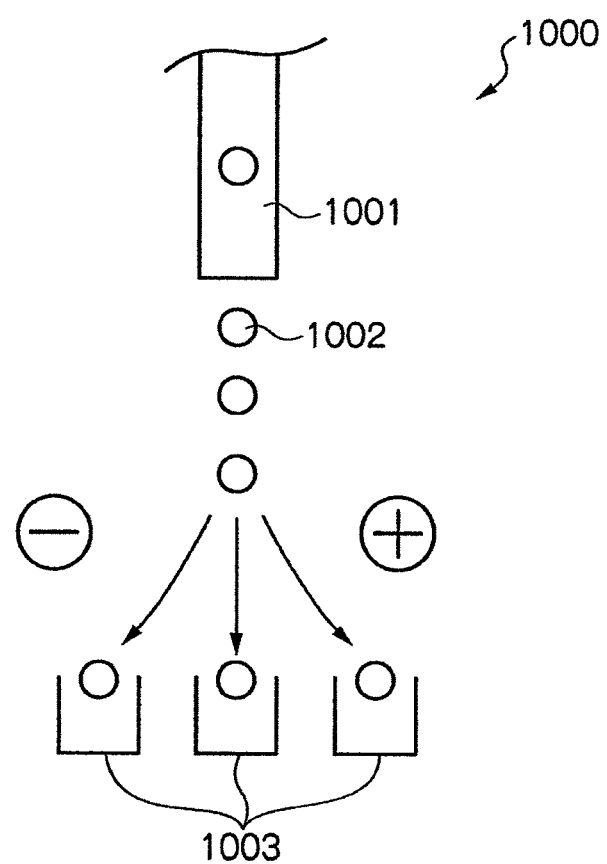
FIG. 17 is a view illustrating a comparative example of a structure of a dispensation part 1000 that is conventionally used.

FIG. 17 illustrates a comparative example of a structure of a dispensation part 1000 that is conventionally used.

After a specimen 1002 is identified, a dispensation part 1000 applies ultrasonic vibration to the specimen 1002 to form liquid droplets. For example, an electric charge of several hundred volts is applied. A voltage of several thousand volts is applied from a deflection plate to divide a drop position of each liquid droplet into a positive pole side and a negative pole side, causing dispensation into a well 1003 in the dispensation part. At the time of dispensation, high frequency vibration and a high voltage of several thousand volts are applied to the specimen 1002. For this reason, when a living cell is used as the specimen, a death rate of the specimen after dispensation is high, and even though the specimen is alive, the normal condition of the specimen is not certainly guaranteed.

On the other hand, using the specimen identification and dispensation device 100 according to the exemplary embodiment of the present invention, such an electric charge or voltage is not applied, and the plate 200 side of the dispensation part 13 is movable in the X-axis direction, the Y-axis direction, and the Z-axis direction. Thus, the specimen can be rapidly dispensed into a predetermined specimen dispensation position without having a bad influence on the specimen. Further, since the position of the nozzle 30 is fixed, the plate 200 side moves. Thus, compared to the case in which the nozzle moves, a problem that the specimen leaks from the nozzle 30 does not rise.

Figure 18:
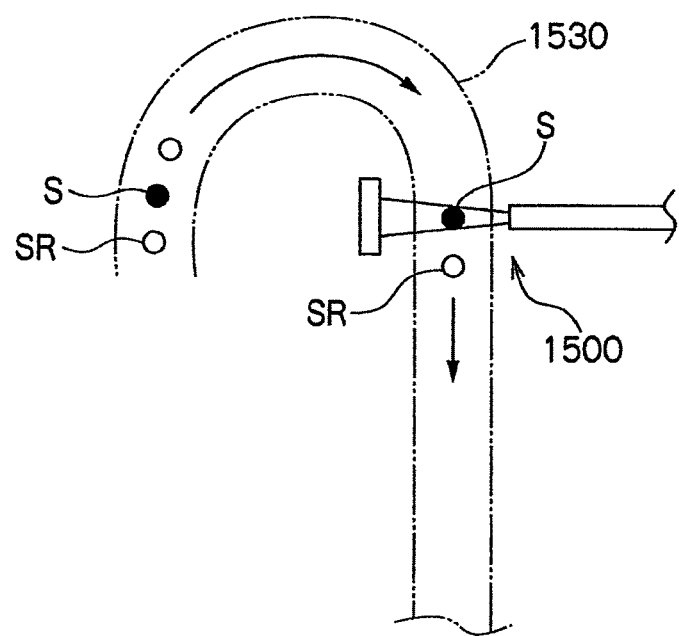
FIG. 18 is a view illustrating a comparative example in which an optical measurement part of a specimen is configured with a curved tube 1530.

As illustrated in FIG. 2, the flow passage formed by the optical measurement device 12 as the identification part and the nozzle 30 is formed in the form of the straight line. Compared to the case in which an optical measurement part 1500 of the specimen S is configured with a curved tube 1530 as in the comparative example illustrated in FIG. 18, the flow velocity of the specimen S can be further stabilized, thereby increasing the degree of accuracy at the time of optical measurement of the specimen.

The specimen identification and dispensation device 10 according to the exemplary embodiment of the present invention includes the optical measurement device 12 that is the identification part for identifying the specimen S by irradiating the exciting light L to the specimen S as a measurement object that is dispersed in the liquid flowing inside the capillary as the flow passage and measuring light information of the specimen S and the dispensation part 13 for dispensing the identified specimen S into the well W that is a dispensation target section through the nozzle 30. The dispensation part 13 is movable three-dimensionally with respect to the identification part 12 and the nozzle 30. Thus, after identification of the specimen S is performed, the specimen S can be rapidly dispensed into a predetermined specimen dispensation position without moving the nozzle 30 side and having a bad influence on the specimen S.

In the specimen identification and dispensation device 10 according to the exemplary embodiment of the present invention, the dispensation target section is a plurality of wells W formed in the plate 200. The culture solution 70 as a storage liquid into which the specimen S is immersed is stored in the well W. The liquid containing the specimen S ejected from the front end opening part 55 of the nozzle 30 comes in contact with the culture solution in the well W and is dispensed. The nozzle 30 can dispense the liquid containing the specimen S without directly contacting the culture solution 70. Thus, after identification of the specimen is performed, the specimen can be rapidly dispensed into a predetermined specimen dispensation position without causing the specimen and the culture solution to be contaminated nor having an influence on the specimen.

In the specimen identification and dispensation device 10 according to the exemplary embodiment of the present invention, the liquid containing the specimen has a hemispherical shape, the specimen is a cell, and the storage liquid in the well is a culture solution. After specimen identification is performed, the cell can be rapidly dispensed into a predetermined specimen dispensation position without causing the culture solution 70 to be contaminated nor having an influence on the cell.

In the specimen identification and dispensation device 10 according to the exemplary embodiment of the present invention, a portion of the nozzle in which the front end opening part is formed is formed with the taper shape. Thus, a situation in which the nozzle 30 comes in contact with the storage liquid in the well W can be greatly reduced. After specimen identification is performed, the specimen can be rapidly dispensed into a predetermined specimen dispensation position without causing contamination nor having an influence on the specimen.

In the specimen identification and dispensation device 10 according to the exemplary embodiment of the present invention, the flow passage of the nozzle 30 is larger than the flow passage of the optical measurement device 12. Thus, when the liquid containing the specimen S flows into the nozzle from the flow passage in the optical measurement device 12, the flow velocity of the liquid containing the specimen S can be reduced. Thus, the flow velocity can be stabilized, and the light information of the specimen S can be obtained with the high degree of certainty.

The specimen identification and dispensation device 10 according to the exemplary embodiment of the present invention includes the supply part 11 for separating the specimen S and supplying the specimen S to the optical measurement device 12. The flow passage of the specimen S formed by the optical measurement device 12 and the nozzle 30 is formed in the form of the straight line. Thus, the flow velocity of the liquid containing the specimen S can be stabilized, and the light information of the specimen S can be obtained with the high degree of certainty.

Figure 13:
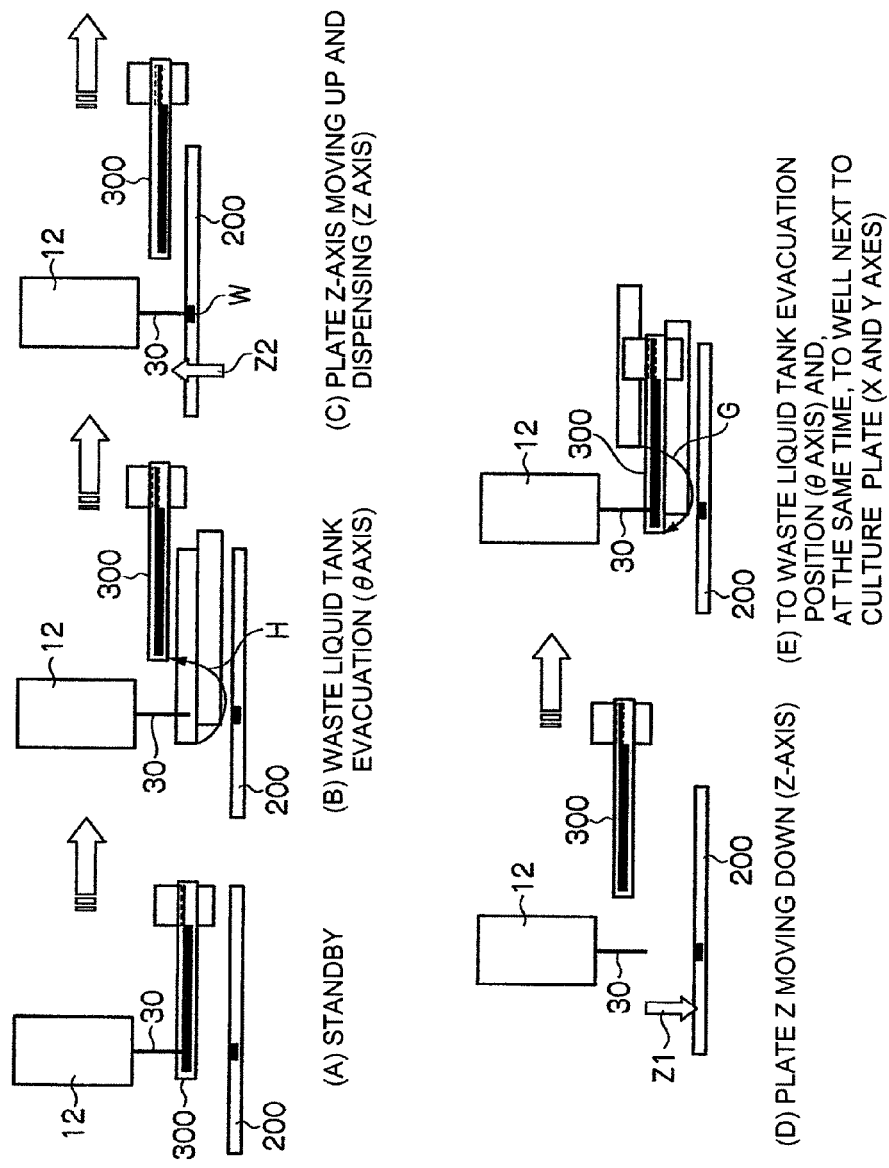
FIG. 13 is views illustrating another example of an operation in which a waste liquid tank returns to a standby position after evacuation.

FIG. 13 illustrates another example of an operation in which the waste liquid tank 300 returns to the standby position after evacuation.

In FIG. 13A, the front end of the nozzle 30 is immerged into the waste liquid in the waste liquid tank 300. In FIG. 13B, as indicated by an arrow H, the waste liquid tank 300 slightly moves down once, so that the front end of the nozzle 30 is evacuated from the inside of the waste liquid tank 300, and thereafter the waste liquid tank 300 moves up and evacuates backward. Thus, the waste liquid tank 300 can evacuate backward without contacting the nozzle 30.

In FIG. 13C, the plate 200 moves up in the Z2 direction, and the front end of the nozzle 30 is inserted into the well W, so that the specimen S can be dispensed. In FIG. 13D, the plate 200 moves down in the Z1 direction, so that the front end of the nozzle 30 is separated from the well W. In FIG. 13E, the waste liquid tank 300 moves in a G direction, and the front end of the nozzle 30 is inserted into the waste liquid tank 300, so that the waste liquid tank 300 returns to the standby position. At the same time, the plate 200 moves so that the specimen can be dispensed into the next well.

Next, a dispensation process of dispensing a target specimen will be explained with reference to FIGS. 1 to 14.

Figure 14:
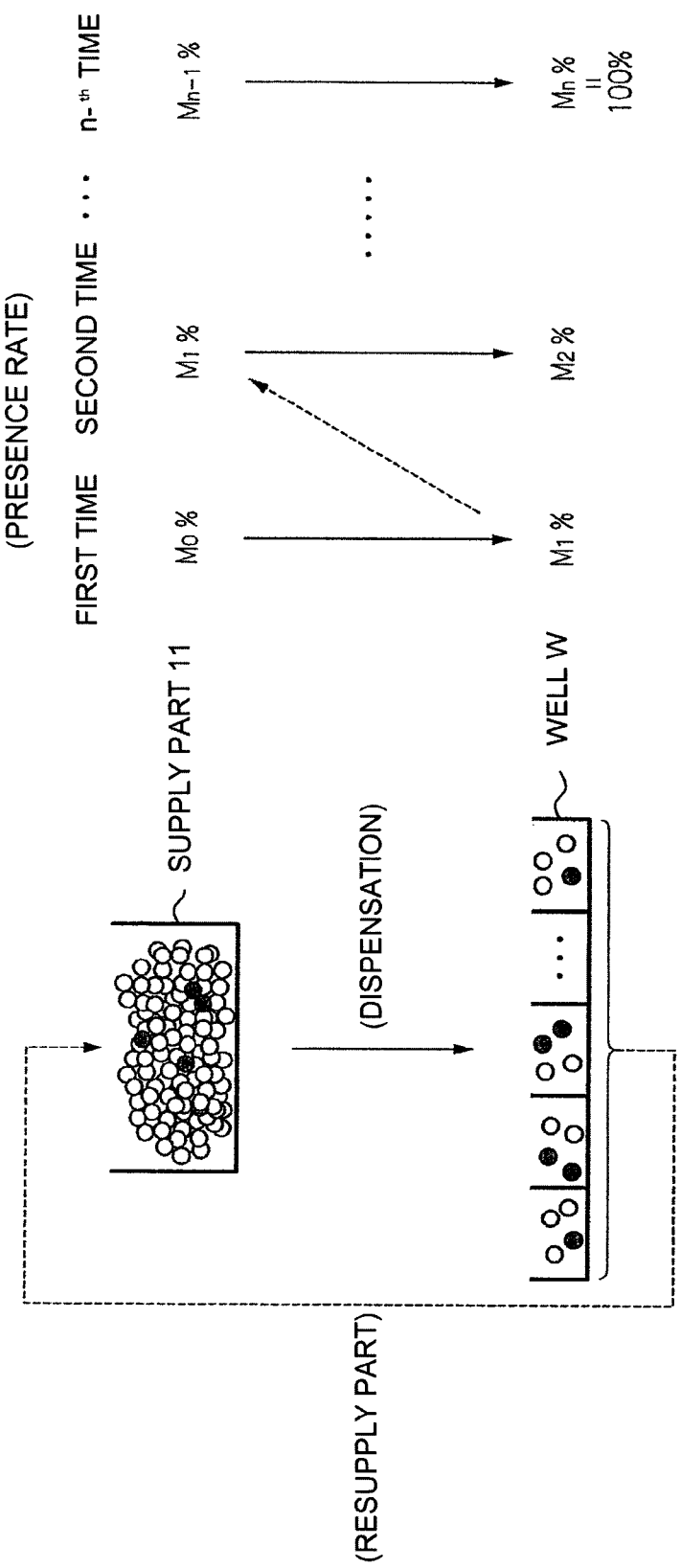
FIG. 14 is a view illustrating a change in presence rate of a target specimen according to a dispensation process.

FIG. 14 is a view illustrating a change in presence rate of the target specimen according to the dispensation process.

Through a one-time dispensation work as illustrated in FIG. 14, the dispensation process increases the presence rate $M_0$ % of the target specimen supplied from the supply part 11 of FIG. 1 to the presence rate $M_1$ % of the specimen S that is to be dispensed into the well W of the dispensation part 12 of FIG. 1.

By repeating the dispensation work through the resupply part twice or more times, the presence rate of the target specimen to be dispensed in to the well W of the dispensation part 13 of FIG. 1 gradually increases. Finally (a result of performing the dispensation work n times: when the concentration of the sample liquid supplied from the supply part 11 of FIG. 1 is within a predetermined range of concentration area), the presence rate $M_n$ % of the target specimen to be dispensed into the well W of the dispensation part 13 becomes 100%, and the specimen is dispensed into the well W one by one.

That is, after the second time, a plurality of specimens containing at least one target specimen dispensed into the well W of the dispensation part 13 of FIG. 1 is supplied to the supply part 11 of FIG. 1 in the next dispensation work, and the sequential dispensation work is executed m times.

The specimen identification and dispensation device 100 according to the exemplary embodiment of the present invention concentrates the sample liquid in a stepwise fashion, that is, increases the presence rate of the target specimen to make the appropriate concentration (the sample liquid concentration) of the specimen contained in the sample liquid and then dispenses the target specimen one by one. Thus, in the dispensation process of dispensing the target specimen, the number of times of the operation work of the dispensation part 13 of FIG. 1 in which the operation time is expended is reduced, thereby reducing the dispensation process time.

Next, a result of an embodiment example of the dispensation process performed through the specimen identification and dispensation device 10 according to the exemplary embodiment of the present invention will be explained with reference to FIGS. 15 and 16.

In the present example, the dispensation process of performing the dispensation work twice and dispensing 10 target cells from among a total of 100,000 cells was performed. FIG. 15 is a view for explaining the embodiment example. FIG. 16 illustrates a result of the dispensation process of the embodiment example.

Figure 15:
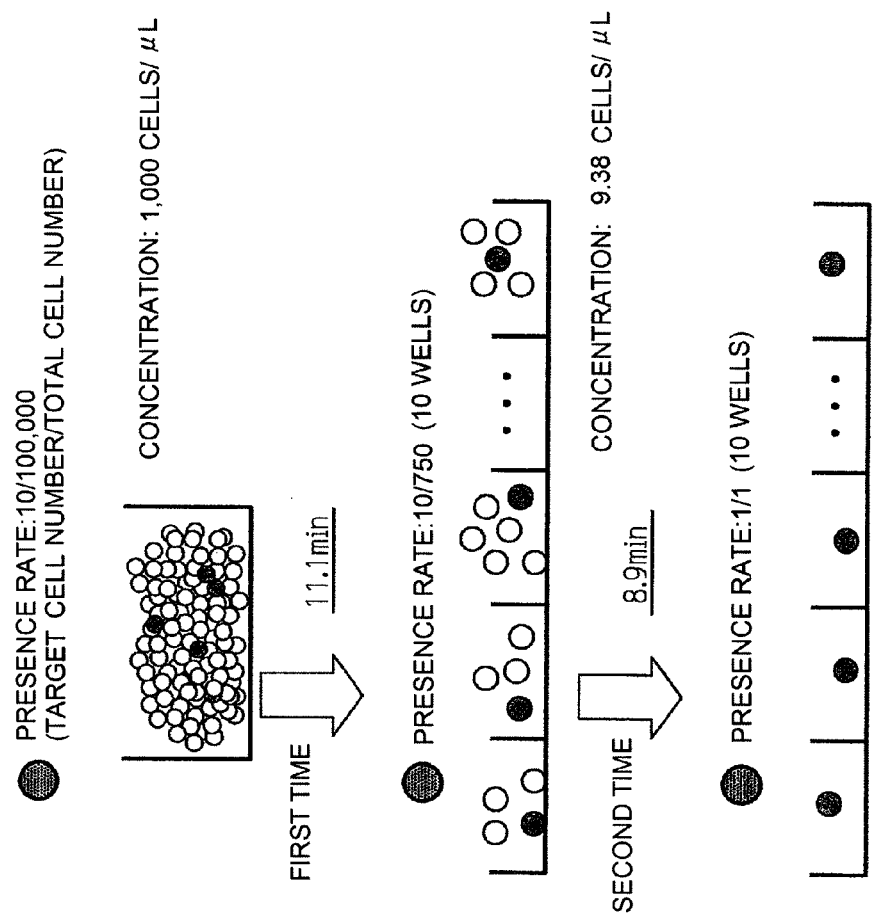
FIG. 15 is a view for explaining an embodiment example.

As illustrated in FIGS. 15 and 16, first, through the first-time dispensation work, the sample liquid amount 100 µl in which the concentration in which total 100,000 cells including 10 target cells are dispersed is 1000 cells/µl was supplied from the supply part 11 of FIG. 1, and 75 cells includes at least one target cell were dispensed into each of 10 well W.

As a result, the presence rate of the target cell in the supply part 11 of FIG. 1 was 0.01%, but the presence rate of the target cell dispensed into the well W of the dispensation part 13 of FIG. 1 became 1.33%. The time expended in the first-time dispensation work was 11.1 minutes. At this time, the storage liquid in the well W was 50 µl, and the liquid amount in the well W was 80 µl.

Next, through the second-time dispensation work, total 750 cells (the cells are dispersed in 80/µl of the sample liquid amount in which the concentration is 9.38 cells/µl) including 10 dispensed target cells was supplied from the supply part 11 of FIG. 1, and one target cell was dispensed into each of 10 wells. As a result, the presence rate of the target cell in the supply part 11 of FIG. 1 was 0.33%, but the presence rate of the target cell dispensed into the well W of the dispensation part 13 of FIG. 1 became 100%. The time expended in the second-time dispensation work was 8.9 minutes.

As a result, in the dispensation process on the total 100,000 cells including 10 target cells, the processing time that was 28 hours in the conventional art was shortened to 20 minutes, and thus it was found that the processing time was greatly reduced.

However, the present invention is not limited to the exemplary embodiments described above, and a variety of modifications can be made.

For example, the light receiving part 42 illustrated in FIG. 1 is disposed at a positions opposite to the optical fiber 40 with the capillary 21 interposed therebetween. However, the present invention is not limited thereto, but the light receiving part 42 may be disposed at a position of a side of the capillary 21 (a position of a direction perpendicular to the paper plane in FIG. 1).

The capillary 21 illustrated in FIGS. 1 and 2 is a hollow member having, for example, a rectangular cross section but may have a cross section of any other shape.

The dispensation part 13 is a plate, but not limited to a plate, and may be a tube or a dish.

The resupply part may not be disposed in the specimen identification and dispensation device as a mechanism, and it is preferable to supply the dispensed specimen to the optical measurement device 12 once again through the resupply part 13.

A signal such as scattered light, transmitted light, and fluorescent light information obtained from the specimen S, for example, the cell can be acquired by using the light receiving part 42.

The transparent member is not limited to a glass plate, and any other transparent material such as a transparent plastic plate may be used.

The nozzle 30 may be not vertical but tilted to the waste liquid tank 300 as illustrated in the drawings.

According to the present invention, the exciting light can be referred to as measurement light or irradiation light.

The optical measurement device of the present invention can be applied to all fields such as a field that requires inspection and analysis on a biological polymer of a gene, an immunity system, protein, an amino acid, and sugar like an engineering field, an agriculture field including food product, agriculture product, and seafood processing, a medicine field, a medical field including hygiene, health, immunity, plague, and heredity, and a physical science field including chemistry and biology.

The invention claimed is:

1. A specimen identification and dispensation apparatus that dispenses a target specimen as an aliquot target from specimens, which are measurement targets, dispersed in as sample liquid flowing in a flow passage, comprising:
   an optical measurement device that measures light information of the specimen by irradiating exciting light onto the specimen and identifies the specimen as a target specimen based on the light information of the measured specimen;
   a dispensation target container that receives, from a nozzle, a dispensed aliquot solution in which one or a plurality of target specimens identified by the optical measurement device is dispersed;
   a supply container from which the specimens dispersed in the sample liquid are provided to the optical measurement device; and
   a controller that controls a resupply path that supplies a liquid containing the target specimens from the dispensation target container to the supply container as the sample liquid to adjust the number of the target specimens as an aliquot object and the number of non-target specimens contained in the aliquot solution to a desired number, based on a sample liquid concentration that is a concentration of the number of specimens contained in the sample liquid in which the specimens are dispersed and an amount of the aliquot solution, wherein the supply container, the optical measurement device, and the nozzle are serially connected such that fluid flowing from the supply container first passes through the optical measurement device before exiting the nozzle.

2. The specimen identification and dispensation apparatus according to claim 1, wherein the amount of the aliquot solution is adjusted based on an amount of the sample liquid and an operation time of the nozzle for performing dispensation.

3. The specimen identification and dispensation apparatus according to claim 1, wherein the dispensation target container receives the aliquot solution a predetermined number of times.

4. The specimen identification and dispensation apparatus according to claim 1, wherein the optical measurement device identifies the specimen based on a plurality of identification setting conditions, and the dispensation target container receives the dispensed aliquot solution based on the plurality of identification setting conditions for identifying the specimen.

5. The specimen identification and dispensation apparatus according to claim 1, wherein at least a portion of the specimen identification and dispensation apparatus is movable three-dimensionally with respect to the nozzle.

6. The specimen identification and dispensation apparatus according to claim 1, wherein the dispensation target container includes a plurality of wells formed in a plate, a storage liquid into which the specimen is immersed is stored in the wells, and the aliquot solution containing the specimen ejected from a front end opening part of the nozzle comes into contact with the storage liquid in the wells and is dispensed without forming a liquid droplet from the nozzle.

7. The specimen identification and dispensation apparatus according to claim 6, wherein the aliquot solution containing the specimen therein is formed in a hemispherical shape at the nozzle front end, the specimen is a cell, and the storage liquid in the well is a culture solution.

8. The specimen identification and dispensation apparatus according to claim 6, wherein a portion of the nozzle that forms the front end opening part is formed in a manner such that an outer diameter thereof is tapered toward the front end opening part.

9. The specimen identification and dispensation apparatus according to claim 1, wherein a flow passage of the nozzle is larger than a flow passage of the optical measurement device.

10. The specimen identification and dispensation apparatus according to claim 1, wherein a flow passage of the specimen formed by the optical measurement device and the nozzle is formed in the form of a straight line until the specimen is dispensed into the dispensation target container.

11. The specimen identification and dispensation apparatus according to claim 1 wherein a presence ratio that is a ratio of a total number of the target specimens with respect to a total number of the specimens contained in the sample liquid in the supply container is adjusted.

12. The specimen identification and dispensation apparatus according to claim 1, wherein when the concentration of the sample liquid containing the target specimen is within a predetermined range of concentration area, the controller adjusts the number of the specimens contained in the aliquot solution to one, and the nozzle dispenses the aliquot solution in which one of the target specimens is dispersed.

13. A specimen identification and dispensation method of dispensing a target specimen as an aliquot target out of specimens, which are measurement targets, dispersed in a sample liquid flowing in a flow passage, comprising:

(a) a supply step of separating the specimen, and dispersing and supplying the specimen into the sample liquid within a supply container;

(b) an identification step of measuring light information of the specimen by irradiating exciting light onto the specimen and identifying the specimen as a target specimen based on the light information of the measured specimen;

(c) a concentration adjustment step of adjusting the number of the specimens in an aliquot solution in which one or a plurality of target specimens identified in the identification step (b) is dispersed;

(d) a dispensation step of dispensing the aliquot solution, which is identified through the identification step (b) and adjusted in number through the concentration adjustment step (c), into a dispensation target container through a nozzle; and (e) a resupply step of supplying a liquid containing the target specimen from the dispensation target container to the supply container of the supply step (a) as the sample liquid, wherein the concentration adjustment step (c) comprises adjusting the number of the target specimens as an aliquot object and the number of non-target specimens in the aliquot solution to desired numbers based on a sample liquid concentration that is a concentration of the number of specimens in the sample liquid in which the specimens are dispersed, and an amount of the aliquot solution, and the sample liquid flows from the supply container of the supply step (a) and through the identification step (b) before exiting the nozzle.

14. The specimen identification and dispensation method according to claim 13, wherein the amount of the aliquot solution is adjusted based on a mechanical operation time of the dispensation step (c) for performing dispensation into the dispensation target container through the nozzle.

15. The specimen identification and dispensation method according to claim 13, wherein the dispensation step (d) comprises dispensing the aliquot solution into the same dispensation target container a predetermined number of times.

16. The specimen identification and dispensation method according to claim 13, wherein the identification step (b) comprises identifying the specimen based on a plurality of identification setting conditions, and the dispensation step (d) comprises performing dispensation into a plurality of dispensation target containers based on the plurality of identification setting conditions for identifying the specimen in the identification step (b).

17. The specimen identification and dispensation method according to claim 13,
wherein a presence ratio that is a ratio of a total number of the target specimens to a total number of the specimens contained in the sample liquid in the supply step (a) is adjusted.

18. The specimen identification and dispensation method according to claim 13,
wherein when the concentration of the sample liquid containing the target specimen is within a predetermined range of concentration area, the concentration adjustment step (c) comprises adjusting the number of the specimens in the aliquot solution to one, and the dispensation step (d) comprises dispensing the aliquot solution in which one of the target specimens is dispersed to one of plural dispensation target containers.

19. The specimen identification and dispensation method according to claim 17, wherein the presence ratio of the target specimens after performing the resupply step is higher than the presence ratio of the target specimens after performing the supply step (a).

20. The specimen identification and dispensation method according to claim 17, wherein the presence ratio after the resupply step (e) is greater than the presence ratio before the resupply step (e).

\* \* \* \* \*